United States Patent [19]

Smith

[11] 4,201,199
[45] May 6, 1980

[54] ENDOSCOPE ATTACHMENT TO A VIEWING INSTRUMENT FOR INSERTION INTO THE UTERINE CAVITY

[76] Inventor: Donald C. Smith, 7442 SE. 22nd, Mercer Island, Wash. 98040

[21] Appl. No.: 869,257

[22] Filed: Jan. 13, 1978

[51] Int. Cl.² .............................................. A61B 1/30
[52] U.S. Cl. .......................................... 128/7; 128/6
[58] Field of Search ................................... 128/3–8; 350/96.26, 96.10, 319; 356/241

[56] References Cited

U.S. PATENT DOCUMENTS

| 1,692,554 | 11/1928 | Leiter | 128/6 |
| 3,051,176 | 8/1962 | Alberti | 128/6 |
| 3,494,354 | 2/1970 | Yokota et al. | 128/6 |
| 3,690,769 | 9/1972 | Mori | 350/96.26 UX |
| 3,809,072 | 5/1974 | Ersek et al. | 350/96.26 UX |

Primary Examiner—Robert W. Michell
Assistant Examiner—Jeffrey W. Tayon
Attorney, Agent, or Firm—Seed, Berry, Vernon & Baynham

[57] ABSTRACT

A glass or plastic tube is sealed and provided with an enlarged bulb of optical clarity and minimum distortion which fits over and is spaced from the end of an endoscope.

2 Claims, 2 Drawing Figures

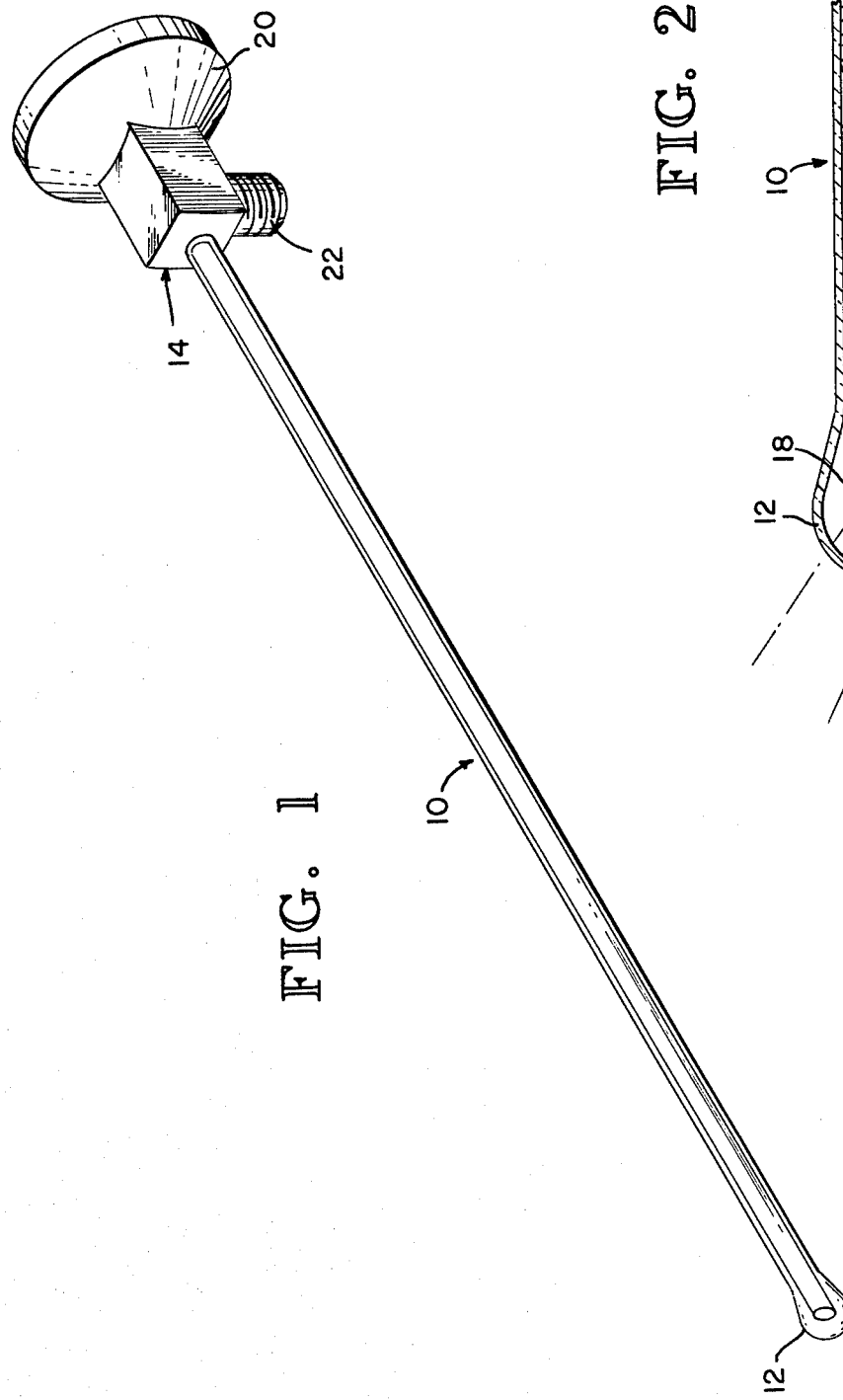
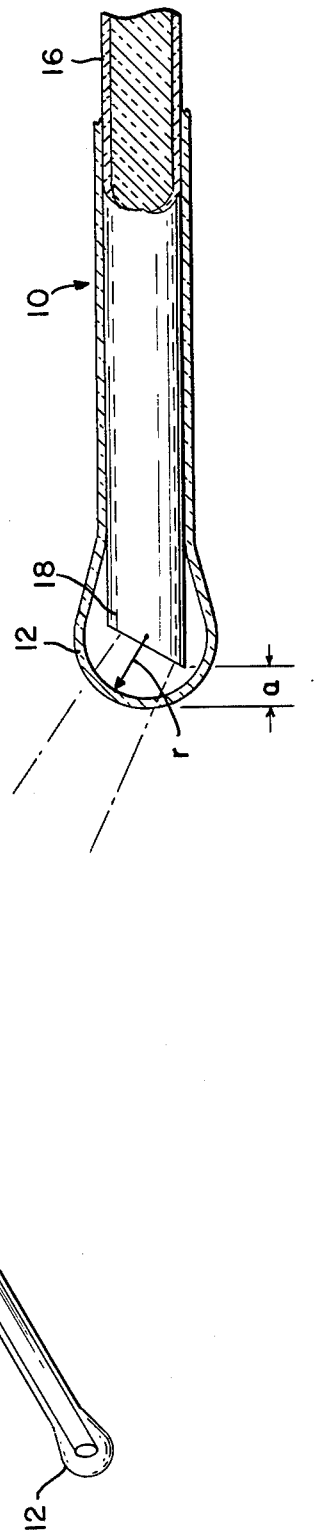

ENDOSCOPE ATTACHMENT TO A VIEWING INSTRUMENT FOR INSERTION INTO THE UTERINE CAVITY

BACKGROUND OF THE INVENTION

Encoscopy, the use of optical instruments to view within body cavities, is employed in many medical specialties. Hysteroscopy is a procedure that enables one to view within the uterine cavity. This is accomplished via the transvaginal route and is carried out either in an operating room setting or in a physician's office, utilizing local anesthetic. In its use today, the most common methods employ a distending fluid (either gaseous, or more commonly, liquid) to distend the uterine cavity thereby offering a more panoramic view within an otherwise mere potential space. Although this method has significant advantages in the view obtained, the complexity and sophistication of the instrumentation and methodology present significant disadvantages as well. In addition to this, there is certain risk inherent in the system of delivering distending fluids into the uterus.

One known device described in the *Southern Surgeon,* Vol. 13, 1947 No. 12 at page 888 and what appears as a similar device in *Journal Gynec. Obst. Biol. Repro.* 1974, 3, 511-520 attempts to improve viewing with the use of a transparent tube fitted over the end of an endoscope. These devices are believed to be unsatisfactory, however, since they provide either lack of support within the tube for the end of the scope, too much optical distortion, or not enough distention of the cavity.

SUMMARY OF THE INVENTIION

The main requirements of a hysteroscope, are: (1) to separate the uterine walls or distend the uterine cavity (which is only a potential cavity) to achieve a viewing space, (2) provide satisfactory optics and light source to achieve the examination, (3) to keep the diameter of the instrument to a satisfactory minimum in order that only minimal dilation of the opening of the uterus (cervix) need be accomplished prior to insertion of the hysteroscope, (4) to use an instrument safe in operation and easily removed from within the cavity.

It is the object of the invention presented to achieve these requirements with a very simple instrument. Basically, the device comprises an attachment at the end of a standard endoscope (or other internally inserted viewing instrument) to distend the viewing cavity to enlarge the viewing area with an optically clear transparent surface of minimal distortion and accurately locating this surface a fixed distance from the viewing end of the scope. Preferably the distending and viewing surface are attached to the end of the scope in such a manner that it is easy to retrieve. Generally this means the attachment should itself protrude from the cavity under examination, should snugly fit over the scope for support if made of glass or other breakable material and should be carried with the scope during insertion and removal. Various other forms of attachment are considered feasible with varying degrees of disadvantage as for example the attachment could be threadably secured to the distal end of the scope rather than extend the length of the scope.

BRIEF DESCRIPTION OF THE DRAWINGS

FIG. 1 is a perspective view of the inventive endoscope attachment mounted on an endoscope.

FIG. 2 is a detailed partial sectional view of the light transmitting and receiving end of the inventive endoscope attachment mounted on an endoscope.

DETAILED DESCRIPTION OF THE INVENTION

The details of the preferred embodiment will now be described. The attachment consists of a glass or plastic tubing 10 that has had one end sealed and blown or otherwise formed into a slight bulb 12. As best shown in FIG. 2, the inside diameter of the tube is approximately 4 mm and the outside diameter, 6 mm. This allows the glass tube to be slipped over a conventional Storz-Hopkins endoscope (Model 27015B) 14 with a snug fit which provides the glass tube with a strong backbone along its length to help insure against breakage. As is well known the endoscope has a light and image transmitting tube 16 having a distal viewing end 18, and an eyepiece 20 and including an eyepiece 20 and a light receiving chamber 22. The length of the glass tubing is such that it abuts against the hub of the Hopkins endoscope (FIG. 1) and projects the distal end of the bulb an accurate distance "a" approximately 2-3 mm beyond the viewing end. The bulb has a radius "r" of preferably 4 mm but a range of 3-4 mm appears to be satisfactory. If the diameter of the bulb gets too small the small radius of curvature causes optical distortion. If the bulb gets too large insertion becomes difficult. The object of the blown bulb is (1) to provide separation of the uterine walls and create a viewing space, (2) to decrease distortion by increasing the diameter of the glass curvature through which one must view and (3) to keep blood or other materials away from the end of the endoscope. The diameter of the bulb is limited however in that the larger the diameter of the instrument, the larger the cervix must be dilated. It is the aim of the procedure to keep this to an acceptable minimum.

In actual production scale, the instrument should be made of non-breakable material when manufactured. The bulb also should provide optical clarity and the curvature should not distort the viewed image. Preferably different sizes and lengths can be used to fit endoscopes made by other manufacturers. The snug fit of the glass tubing over the image transmitting tube 16 and the abutment of the end of the glass tubing against the hub of the endoscope provides a coupling between the glass tubing and endoscope for accurate placement and ease of insertion and removal.

I claim:

1. An attachment for an endoscope of the type to be inserted through the cervix into the uterine cavity and having a light and image transmitting tube with an eyepiece end for viewing through the tube, said eyepiece end having a portion of increased transverse dimension with respect to the transverse dimension of said tube, and a distal viewing end for location close to the uterine cavity wall under investigation, said attachment comprising:

a rigid, transparent, generally spherical bulb of a diameter substantially greater than the diameter of the light and image transmitting tube for separating the walls of the uterine cavity, said bulb having a relatively thin wall and an inside radius of approximately between 3 and 4mm, said bulb being carried by the end of a rigid outer tube to which said bulb is smoothly faired, said outer tube having an inside diameter approximately equal to the outside diameter of said light and image transmitting tube so that said outer tube snugly fits over said light and image transmitting tube, the length of said outer tube being such that when the end of said outer tube opposite said bulb abuts the portion of increased diameter of said eye piece end, the distal end of the outside surface of said bulb is spaced approximately between 2 to 3 mm beyond the distal end of said light and image transmitting tube.

2. The attachment of claim 1, said bulb being an integral part of the material of said outer tube.

* * * * *